US007714573B2

(12) United States Patent
Edwards

(10) Patent No.: US 7,714,573 B2
(45) Date of Patent: May 11, 2010

(54) NUCLEAR QUADRUPOLE RESONANCE LOGGING TOOL AND METHODS FOR IMAGING THEREWITH

(75) Inventor: Carl Edwards, Katy, TX (US)

(73) Assignee: Baker Hughes Incorporated, Houston, TX (US)

( * ) Notice: Subject to any disclaimer, the term of this patent is extended or adjusted under 35 U.S.C. 154(b) by 187 days.

(21) Appl. No.: 11/724,956

(22) Filed: Mar. 16, 2007

(65) Prior Publication Data

US 2008/0224696 A1  Sep. 18, 2008

(51) Int. Cl.
*G11V 3/00* (2006.01)
(52) U.S. Cl. ..................... 324/303; 324/300
(58) Field of Classification Search ......... 324/300–322; 702/7
See application file for complete search history.

(56) References Cited

U.S. PATENT DOCUMENTS

| | | | |
|---|---|---|---|
| 4,710,713 A | | 12/1987 | Strikman |
| 4,710,714 A | * | 12/1987 | Weitkamp et al. ............ 324/307 |
| 4,987,368 A | * | 1/1991 | Vinegar ..................... 324/303 |
| 5,233,300 A | | 8/1993 | Buess et al. |
| 5,365,171 A | | 11/1994 | Buess et al. |
| 5,712,566 A | | 1/1998 | Taicher et al. |
| 5,814,987 A | * | 9/1998 | Smith ......................... 324/300 |
| 6,104,190 A | | 8/2000 | Buess et al. |
| 6,166,541 A | * | 12/2000 | Smith et al. ................. 324/300 |
| 6,247,542 B1 | | 6/2001 | Kruspe et al. |
| 6,366,089 B1 | * | 4/2002 | Poitzsch et al. ............. 324/303 |
| 6,373,248 B1 | * | 4/2002 | Poitzsch et al. ............. 324/303 |
| 6,522,135 B2 | | 2/2003 | Miller et al. |
| 6,686,737 B2 | * | 2/2004 | Kruspe et al. ............... 324/303 |
| 6,952,096 B2 | * | 10/2005 | Freedman ................... 324/303 |
| 7,265,550 B2 | | 9/2007 | Laubacher et al. |
| 7,425,827 B2 | * | 9/2008 | Chen et al. .................. 324/303 |
| 2003/0071619 A1 | | 4/2003 | Sauer et al. |
| 2005/0162163 A1 | | 7/2005 | Mikhaltsevitch et al. |
| 2007/0244648 A1 | * | 10/2007 | Chen .......................... 702/11 |
| 2008/0073122 A1 | | 3/2008 | Blanz et al. |
| 2008/0234937 A1 | * | 9/2008 | Fang ............................ 702/7 |

FOREIGN PATENT DOCUMENTS

| | | |
|---|---|---|
| WO | 9906854 A3 | 2/1999 |
| WO | 9919740 A1 | 4/1999 |
| WO | 9945409 A1 | 9/1999 |

OTHER PUBLICATIONS

Hoult, D. I. (1979). "Rotating Frame Zeugmatography." Journal of Magnetic Resonance 33: 183-97.
Das, T. P. and E. L. Hahn (1958). Nuclear Quadrupole Resonance. New York, Academic Press, Inc. pp. 1-209.

(Continued)

*Primary Examiner*—Brij B Shrivastav
(74) *Attorney, Agent, or Firm*—Cantor Colburn LLP

(57) ABSTRACT

An instrument for investigating properties of an earth formation includes a body housing a nuclear quadrupole resonance (NQR) probe, the probe having at least one coil wound around a core material and an electronics coupling, the body being adapted for insertion into a wellbore within the earth formation. A method and computer program product are provided.

17 Claims, 12 Drawing Sheets

OTHER PUBLICATIONS

Smith, J. A. S. (1971). "Nuclear Quadrupole Resonance Spectroscopy. General Principles." Journal of Chemical Education 48(1): 39-49.

Buslaeva, Y. A., E. A. Kravqenko, et al. (1987). "Nuclear quadrupole resonance in inorganic chemistry." Coordination Chemistry Reviews 82: 9-231.

Marino, R. A. and S. M. Klainer (1977). "Multiple spin echoes in pure quadrupole resonance." Journal of Chemical Physics 67(7): 3388-3389.

Lee, K. and W. Anderson (1967). Nuclear Spins, Moments, and Magnetic Resonance Frequencies. CRC Handbook of Chemistry and Physics. R. C. Weast and M. J. Astle. Boca Raton, Florida, CRC Press, Inc.: E66-68.

Huang, W. T. (1962). Petrology. New York, McGraw-Hill Book Company. Chapter 1. pp. 1-20.

Klainer, S. M., T. B. Hirschfeld, et al., "Fourier Transform Nuclear Quadrupole Resonance Spectroscopy", Fourier, Hadamard, and Hilbert Transforms in Chemistry, A. G. Marshall, New York Plenum Press: 147-182 (1982).

Petersen, G. L., "Pulsed nuclear quadrupole resonance instrumentation and study of the 14N spectrum and relaxation in sodium nitrite", Physics, Providence, Brown University: 1-221 (1975).

Cook, J. C. and J. R. Clements (1970). NQR borehole logging for evaporite minerals Third Symposium on Salt; vol. 2, Evaporated salt, solar salt, economic aspects, salt applications, rock physics-mechanics, subsidence, geophysics, hydraulic fracturing, mining J. L. D. Rau. Cleveland, OH N. Ohio Geol. Soc.: 353-356.

Marino, R. A., H. Wenk, et al. (1980). "Proposed applications of NQR techniques to the geosciences." Journal of Molecular Structure 58: 445-457.

Schempp, E., S. M. Klainer, et al. (1980). An Evaluation of Nuclear Quadrupole Resonance (NQR) Techniques for the In-Situ Measurement of Stress/Strain in Salt. Earth Sciences Division Annual Report, Lawrence Berkeley Laboratory. Report Analytic. No. LBL-12100.

Schempp, E., J. B. Murdoch, et al. (1981). Measurement of in-situ stress using NQR/NMR. Earth Sciences Division 1981 Annual Report, Lawrence Berkeley Laboratory. Report Analytic. No. LBL-13600.

* cited by examiner

Chlorite

○ Oxygens  ○ Hydroxyls  ● 
○ and ● Silicon, occasionally aluminum

FIG. 6B
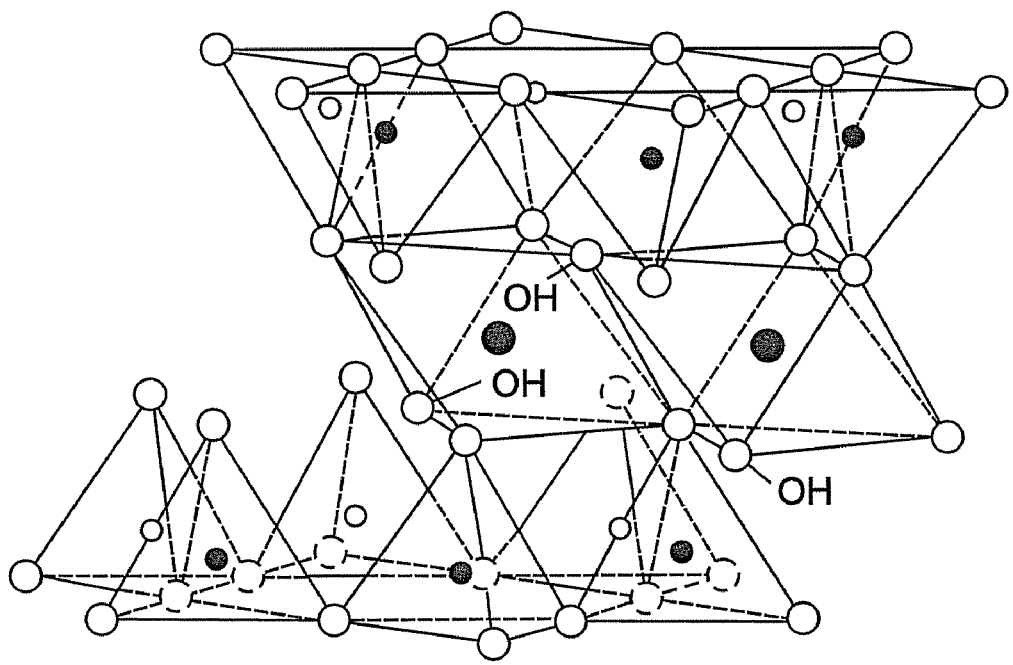
Exchangeable cations
nH₂O
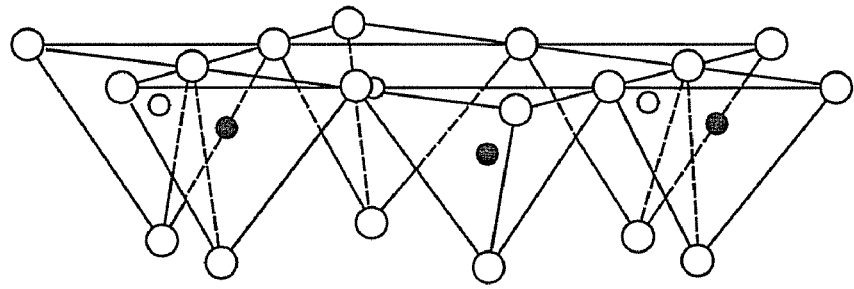
Smectite
○ Oxygens
○ Hydroxyls (OH)
● Aluminum, Iron, magnesium
○ and ● Silicon, occasionally aluminum Kaolinite ○ Oxygens
○ Hydroxyls
● Aluminums
● ○ Silicons

FIG. 7A

| Mineral | Dana Class | Group | Site Symmetry Nuclei | | $Q_{cc}$ $e^2qQ/h$ MHz | $\eta$ | SOQE $Q_{cc}(1+\eta^2/3)^{1/2}$ MHz | $\nu_H$ MHz | Frequencies $\nu_L$ MHz |
|---|---|---|---|---|---|---|---|---|---|
| Albite | Tectosilicate | Plagiolase | 23 Na | | 3.29 | 0.62 | 3.494 | 0.437 | |
| Tugupite | Tectosilicate | Sodalite | 23 Na | | 1.27 | 0.48 | | 0.165 | |
| Diopside | Inosilicate | Clinopyroxenes | 25 Mg | | 2.1 | 0.75 | | | 0.468 |
| Spinel | Multiple Oxides | Aluminum | 25 Mg | | 0.4 | | 2.288 | 0.12-0.092 | 0.092-0.060 |
| Akermanite | Sorosilicate | Mellitte | 25 Mg | | 2.8 | 0.2 | 2.819 | 0.833 | 0.438 |
| Andalusite | Nesosilicate | Andalusite | 27 Al | 5 | 5.73 | 0.7 | 6.180 | 1.593 | 1.231 |
| Andalusite | Nesosilicate | Andalusite | 27 Al | 6 | 15.5 | 0 | 15.500 | 4.650 | 2.325 |
| Kyanite | Nesosilicate | Kyanite | 27 Al | 6 | 3.7 | 0.89 | 4.160 | 0.996 | 0.909 |
| Kyanite | Nesosilicate | Kyanite | 27 Al | 6 | 6.53 | 0.59 | 6.898 | 1.849 | 1.296 |
| Kyanite | Nesosilicate | Kyanite | 27 Al | 6 | 9.37 | 0.38 | 9.593 | 2.737 | 1.611 |
| Kyanite | Nesosilicate | Kyanite | 27 Al | 6 | 10.04 | 0.27 | 10.161 | 2.970 | 1.621 |
| Sillimanite | Nesosilicate | Sillimanite | 27 Al | 4 | 6.77 | 0.53 | 7.082 | 1.934 | 1.290 |
| Sillimanite | Nesosilicate | Sillimanite | 27 Al | 6 | 8.93 | 0.46 | 9.244 | 2.578 | 1.621 |
| Topaz | Nesosilicate | Dana | 27 Al | 6 | 1.67 | 0.38 | 1.710 | 0.488 | 0.287 |
| Topaz | Nesosilicate | Dana | 27 Al | 6 | 1.5918 | 0.7 | 1.718 | 0.442 | 0.343 |
| Topaz | Nesosilicate | Dana | 27 Al | 6 | 1.6506 | 0.5 | 1.718 | 0.474 | 0.308 |
| Cookeite | Phyllosilicate | Chlorite | 27 Al | 4 | | | 3.100 | 0.930-0.710 | 0.710-0.0465 |
| pennine | Phyllosilicate | Chlorite | 27 Al | 6 | | | | 0.840-0.641 | 0.641-0.420 |
| pennine | Phyllosilicate | Chlorite | 27 Al | | 2.8 | | | 0.420-0.321 | 0.321-0.210 |
| Kaolinite | Phyllosilicate | Kaolinite | 27 Al | | 1.4 | | 3.785 | 0.986 | 0.742 |
| Kaolinite | Phyllosilicate | Kaolinite | 27 Al | | 3.53 | 0.67 | 3.312 | 0.768 | 0.750 |
| Ephesite | Phyllosilicate | Mica | 27 Al | | 2.89 | 0.97 | 2.820 | 0.846-0.646 | 0.646-0.432 |
| Interlake illite | Phyllosilicate | Mica | 27 Al | | | | 3.000 | 0.900-0.687 | 0.687-0.450 |

| | | | | | | | |
|---|---|---|---|---|---|---|---|
| margarite | Phyllosilicate | Mica | | | | 1.260-0.962 | 0.962-0.630 |
| margarite | Phyllosilicate | Mica | | | | 1.890-1.433 | 1.433-0.945 |
| Muscovite | Phyllosilicate | Mica | 6 | 4.2 | | | |
| muscovite | Phyllosilicate | Mica | 6 | 6.3 | | | |
| muscovite | Phyllosilicate | Mica | 6 | 3.554 | 0.26 | 3.595 | 1.052 | 0.572 |
| Muscovite | Phyllosilicate | Mica | 4 | 2.1 | | | 0.630-0.481 | 0.481-0.315 |
| Wind River Illite | Phyllosilicate | Mica | 6 | 2.2 | | | 0.660-0.504 | 0.504-0.330 |
| Allt Ribhein saponite | Phyllosilicate | Mica | | 3.5548 | 0.27 | 3.596 | 1.052 | 0.573 |
| Ballarat saponite | Phyllosilicate | Smectite | | | | 2.370 | 0.711-0.543 | 0.543-0.356 |
| Black Jack beidellite | Phyllosilicate | Smectite | | | | 3.200 | 0.960-0.733 | 0.733-0.480 |
| Rectorite | Phyllosilicate | Smectite | | | | 2.560 | 0.768-0.586 | 0.586-0.384 |
| Syn montmorillonite | Phyllosilicate | Smectite | | | | 2.540 | 0.762-0.582 | 0.582-0.381 |
| Synthetic saponite | Phyllosilicate | Smectite | | | | 2.280 | 0.684-0.522 | 0.522-0.342 |
| Vermiculite | Phyllosilicate | Smectite | | | | 2.780 | 0.834-0.637 | 0.637-0.417 |
| | Phyllosilicate | Smectite | | | | 2.900 | 0.870-0.664 | 0.664-0.435 |
| | Phyllosilicate | Vermiculite | | | | 2.910 | 0.873-0.667 | 0.667-0.437 |
| Corundum | Simple Oxides | Corundum | 6 | 2.39 | 0 | 2.390 | 0.717 | 0.358 |
| Zoisite | Sorosilicate | Dana | 6 | 8.05 | 0.46 | 8.329 | 2.325 | 1.459 |
| Zoisite | Sorosilicate | Dana | 6 | 18.5 | 0.16 | 18.579 | 5.522 | 2.851 |

FIG. 7B

| | | | | | | |
|---|---|---|---|---|---|---|
| Natrolite | Tectosilicate | Natrolite | 27 Al | 4 | 1.66 | 0.5 | 1.728 | | 0.477 | 0.309 |
| Albite | Tectosilicate | Plagioclase | 27 Al | 4 | 3.29 | 0.62 | 3.494 | | 0.927 | 0.667 |
| Albite | Tectosilicate | Plagioclase | 27 Al | 4 | 3.37 | | | | 1.011 | 0.505 |
| Anorthite | Tectosilicate | Plagioclase | 27 Al | 4 | 8.42 | 0.66 | 9.011 | | 2.357 | 1.758 |
| Anorthite | Tectosilicate | Plagioclase | 27 Al | 4 | 2.66 | 0.66 | 2.847 | | 0.744 | 0.555 |
| Anorthite | Tectosilicate | Plagioclase | 27 Al | 4 | 7.25 | 0.76 | 7.917 | | 1.995 | 1.627 |
| Anorthite | Tectosilicate | Plagioclase | 27 Al | 4 | 6.81 | 0.65 | 7.274 | | 1.909 | 1.412 |
| Anorthite | Tectosilicate | Plagioclase | 27 Al | 4 | 6.3 | 0.88 | 7.066 | | 1.699 | 1.538 |
| Anorthite | Tectosilicate | Plagioclase | 27 Al | 4 | 5.44 | 0.42 | 5.598 | | 1.580 | 0.960 |
| Anorthite | Tectosilicate | Plagioclase | 27 Al | 4 | 4.9 | 0.75 | 5.340 | | 1.351 | 1.092 |
| Anorthite | Tectosilicate | Plagioclase | 27 Al | 4 | 4.32 | 0.53 | 4.518 | | 1.235 | 0.822 |
| Microcline | Tectosilicate | Plagioclase | 27 Al | 4 | 3.22 | 0.21 | 3.244 | | 0.958 | 0.506 |
| Tugupite | Tectosilicate | Sodalite | 27 Al | 4 | 1.7 | 0.19 | 1.710 | | 0.506 | 0.265 |
| xantophyllite | | | 27 Al | 4 | 2.8 | | | | 0.840-0.641 | 0.641-0.420 |
| xantophyllite | | | 27 Al | 6 | 2 | | 2.940 | | 0.600-0.458 | 0.458-0.300 |
| Zemplini I/S | | | 27 Al | | | | | | 0.882-0.674 | 0.674-0.441 |

FIG. 7C

| FIG. 7A |
|---|
| FIG. 7B |
| FIG. 7C |

FIG. 7

FIG. 11
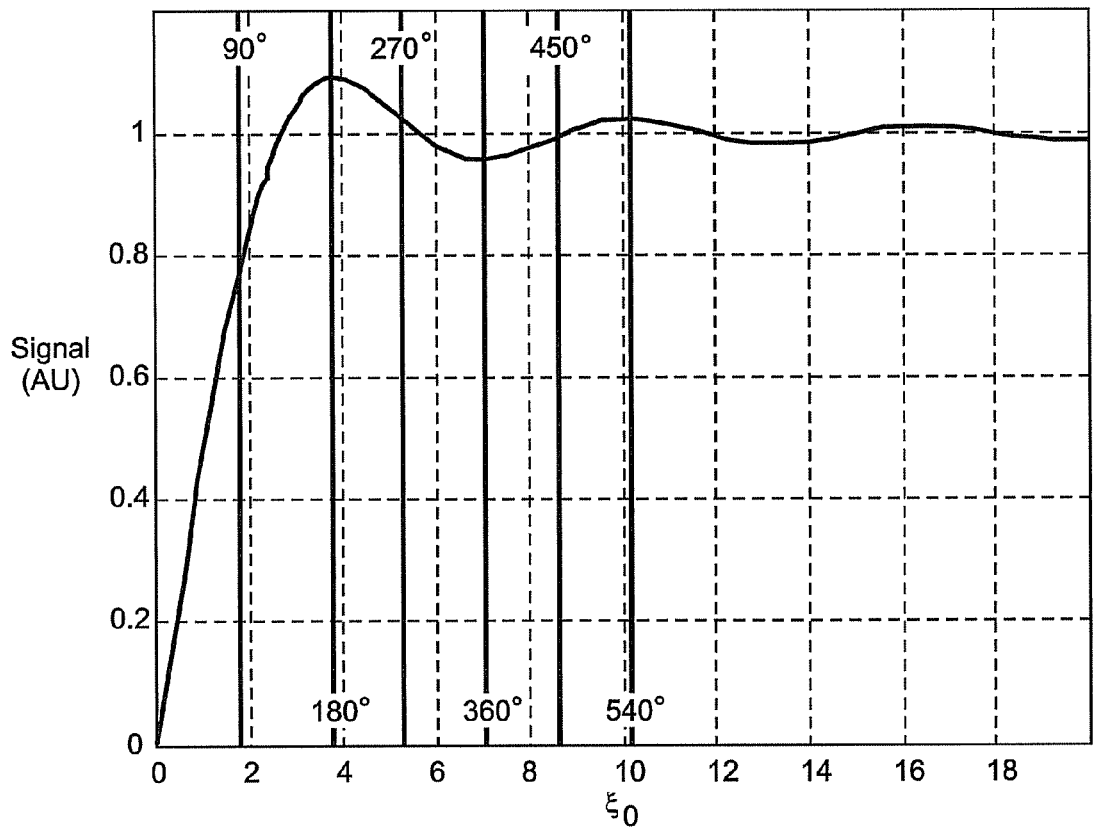
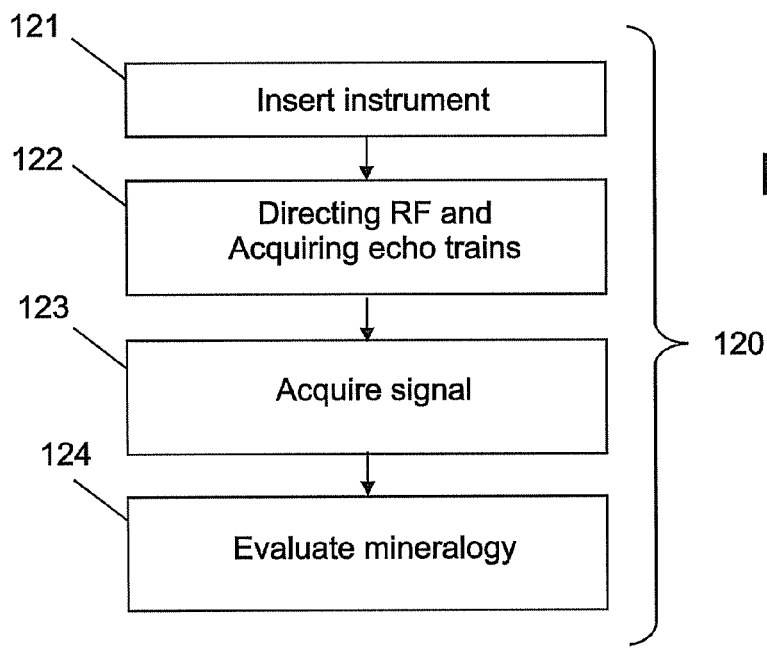
FIG. 12

NUCLEAR QUADRUPOLE RESONANCE LOGGING TOOL AND METHODS FOR IMAGING THEREWITH

BACKGROUND OF THE INVENTION

1. Field of the Invention

This invention relates to imaging of subterranean formations with logging tools, and more particularly to the use of nuclear quadrupole resonance phenomena for ascertaining properties of subterranean materials.

2. Background of the Related Art

As the aggressive search for various minerals and geologic deposits continues unabated, the techniques for subterranean exploration have become increasingly sophisticated. Improved search capabilities requires improvements in the abilities to evaluate materials such as formation fluids in-situ.

Nuclear Quadrupole Resonance (NQR) is a well known technique for identifying and evaluating materials. Nuclear Quadrupole Resonance (NQR) is a phenomenon in the general class of magnetic resonance. Like nuclear magnetic resonance (NMR) and electron spin resonance (ESR), NQR makes use of a resonant exchange of energy between the spin of each nuclei and the environment. This exchange can be detected and used to estimate the properties of the spin-environment interaction and therefore obtain information about the environment in which the nuclei are located. Like NMR and ESR, in NQR the resonant exchange uses a radio-frequency magnetic field. However, unlike NMR and ESR, the resonance condition for NQR does not require an external magnetic field. Rather, the energy of any particular spin state depends on the electric field gradient at the site of the spin. While NMR and ESR depend on magnetic interactions with the magnetic dipole moment of the spin, NQR depends on interactions with both the magnetic dipole and the electric quadrupole moments of the spin. For this reason, NQR phenomena are more complicated to interpret than NMR. Accordingly, use of NQR has not been explored nearly to the extent of NMR.

In recent years, the possibility of using NQR for detection of chemical explosives has been explored. Research in this respect has been sparked by the proliferation of plastic anti-personnel mines. Current techniques for explosives detection relies upon known characteristics of typical explosives. For example, Nitrogen is a common chemical component of explosives. Conveniently for NQR measurements, nitrogen-14 (N-14) has a nuclear spin of one (1) and is almost 100% abundant. Explosives detection using NQR typically calls for use of a radiofrequency (RF) surface coil to detect the NQR resonance of the $^{14}$N nuclei. The resonant frequency obtained can indicate whether $^{14}$N nuclei are in an explosive compound and possibly what kind of explosive is involved. The amplitude of the resonance can indicate the amount of explosive as well.

Imaging of materials is also possible with NQR. In fact, NQR imaging has some advantages over NMR (at least for some materials) because the NQR resonant lines in zero field are more narrow than the resonant lines using NMR at high field.

The principle method used in NQR imaging is derived from rotating-frame zeugmatography. (Hoult 1979). In this method, an RF field gradient is applied to a target volume and the location of the spins is encoded either in the phase of the signal or the amplitude. Images using rotating-frame NQR imaging techniques have been made of such diverse materials such as arsenolite ($^{75}$As), copper oxide ($^{63}$Cu) and boric acid ($^{11}$B). A summary of NQR imaging can be found in various references.

Some geological applications of NQR have already been suggested (reference may be had to Marino, Wenk et al. 1980; Schempp, Klainer et al. 1980; and Schempp, Murdoch et al. 1981). These applications include in-situ estimates of stress, in-situ elemental analysis of minerals, and characterization of phase transitions in minerals. However, no methods for accomplishing these suggestions have been developed as yet.

Elemental analysis of minerals is possible because the resonance frequency of the NQR signal is highly dependent on the quadrupole coupling constant (QCC) of the probe nucleus with the mineral lattice. Different elements will have different resonant frequencies. In fact, isotopes of the same element can have different frequencies even when residing in identical crystal sites.

One element of particular importance to geologists is aluminum. Aluminum-27 ($^{27}$Al) has a spin of $^5/_2$ and is 100% abundant. In a pure sandstone reservoir, the amount of aluminum is directly related to the reservoir's clay content. However, in reservoirs with many mineral types, estimates of the aluminum content might be reduced, with a caveat that the resonant frequency of the aluminum also depends in which mineral the atoms of aluminum reside. With this in mind, it may be possible not only to estimate that total amount of aluminum in the reservoir but also estimate mineral content in situ by an analysis of NQR spectra.

In principle, one could also measure NQR spectra for other isotopes such as $^{35}$Cl, $^{23}$Na, $^{25}$Mg, and $^{43}$Ca to obtain detailed information regarding the mineral composition of subterranean materials, including rock and fluids.

What are needed are techniques for applying NQR technologies to subterranean exploration.

SUMMARY OF THE INVENTION

Disclosed is an instrument for investigating properties of an earth formation, the instrument including: a body housing a nuclear quadrupole resonance (NQR) probe, the probe consisting essentially of at least one coil and an electronics coupling, the body being adapted for insertion into a wellbore within the earth formation.

Also disclosed is a method for investigating properties of an earth formation, the method including: selecting an instrument including a body housing a nuclear quadrupole resonance (NQR) probe, the probe consisting essentially of at least one coil and an electronics coupling, the body being adapted for insertion into a wellbore within the earth formation; disposing the instrument within a wellbore; directing a radiofrequency (RF) signal into the formation; acquiring a NQR signal from the formation; and interpreting the NQR signal to determine the properties.

Further disclosed is a computer program product stored on machine readable media including instructions for investigating properties of an earth formation, the instructions including: directing a radiofrequency (RF) signal into the formation; acquiring a NQR signal from the formation; and interpreting the NQR signal to determine the properties.

Examples of certain features of the invention have been summarized here rather broadly in order that the detailed description thereof that follows may be better understood and in order that the contributions they represent to the art may be appreciated. There are, of course, additional features of the invention that will be described hereinafter and which will form the subject of the claims appended hereto.

BRIEF DESCRIPTION OF THE DRAWINGS

For a detailed understanding of the present invention, reference should be made to the following Detailed Description of the Invention, taken in conjunction with the accompanying drawings, in which like elements have been given like numerals, wherein:

FIG. 7 provides quadrupolar properties of various minerals;

FIG. 11 depicts signal intensity as a function of flip angle at a borehole wall; and FIG. 12 is a flow chart depicting an exemplary method for performing an NQR evaluation.

DETAILED DESCRIPTION OF THE INVENTION

Figure 1:
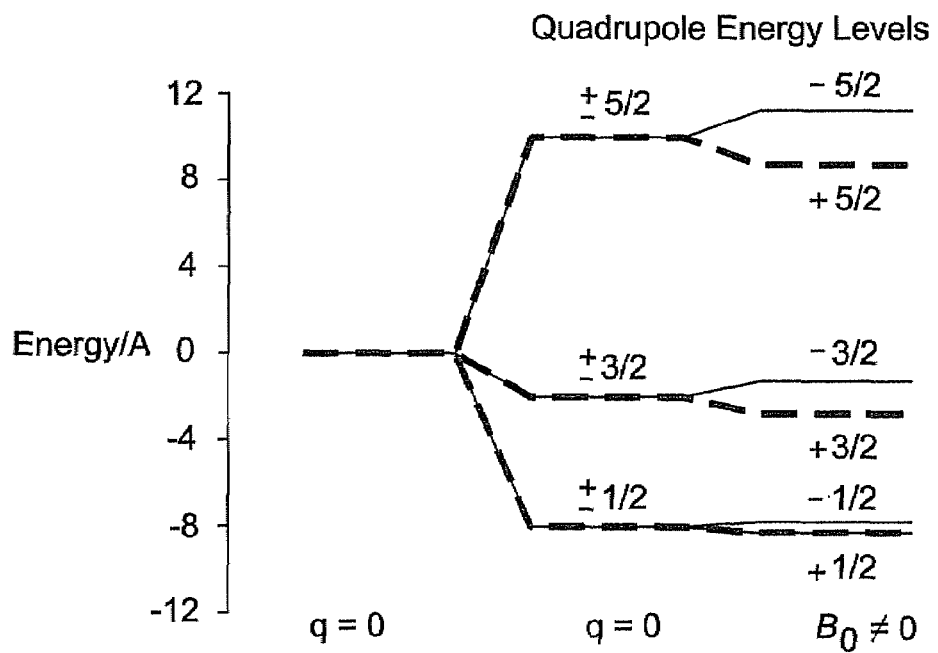
FIG. 1 depicts quadrupolar energy levels in a zero magnetic field.

The teachings herein provide for use of nuclear quadrupole resonance (NQR) technology in subterranean applications. In typical embodiments, the subterranean applications involve use of a well logging tool for mineral exploration. In order to provide proper context for these teachings, this disclosure provides readers with: I. an introduction; II. a review of NQR; III. an evaluation of mineralogy; IV. a review of nuclear magnetic resonance (NMR) and NQR properties of certain minerals; and, V. an introduction to aspects of well logging devices suited for NQR applications.

I. Introduction. Nuclear Quadrupole Resonance (NQR) is a technique related to nuclear magnetic resonance (NMR). NQR provides for detecting atoms whose nuclei have a nuclear quadrupole moment. Examples include nitrogen-14 (N-14), chlorine-35 (Cl-35) and copper-63 (Cu-63). Unlike NMR, NQR measurements are performed in an environment without a static magnetic field (such as a magnetic field generated by an application of direct current (DC)). Accordingly, NQR is sometimes called "zero-field NMR." One skilled in the art will note that many transition frequencies of nuclei that are relevant to NQR measurements depend upon temperature.

The NQR phenomenon and the response to a radiofrequency (RF) pulse is similar to that of an NMR system. Similarity can be shown through the use of quantum mechanical operators such as the NMR vector model for magnetization, although this model is not entirely valid for this purpose. The resonant frequency for NQR depends on the quadrupole coupling constant and the asymmetry parameter through a $3^{rd}$ order secular equation.

The magnetization produced after a single on-resonance pulse is shown to be proportional to the resonant frequency. Like NMR, the amplitude in NQR depends on the product length and strength of the applied RF magnetic field. This is not periodic and varies approximately like a first order Bessel function. Nevertheless, pulse lengths equivalent to angles of about 90° and about 180° (as well as other angles) can be identified.

The disclosure provided herein shows that NQR may be used advantageously to identify certain minerals as may be frequently encountered in subterranean exploration. Further certain simplifications of present day NMR technologies may be used. The application of NQR in subterranean exploration may be used to collect mineralogy data that is of a high quality (i.e., of a high signal-to-noise ratio).

II. Nuclear Quadrupole Resonance Review. This section provides a brief review of the NQR phenomenon. There are a number of books and review articles that describe NQR in general terms. General references include Das and Hahn 1958; Smith 1971; Klainer, Hirschfeld et al. 1982 and Buslaeva, Kravqenko et al. 1987.

In nature there are about thirty (30) non-radioactive nuclear isotopes that have a spin of (½). There are over eighty (80) isotopes with spin of (1) or greater. (Lee and Anderson 1967). As such, a significant number of nuclei that can be used for magnetic resonance have a quadrupole moment. In NMR well logging, the proton ($^1H$) and sodium-23 (Na-23) are of significant interest. For the purpose of NQR well logging and the teachings herein, another isotope, aluminum-27 (Al-27) is reviewed with particular detail. This is due, in part, to the fact that Al-27 is common in minerals and 100% abundant.

Note, that as used herein, certain conventions and notations have been adopted. A non-exhaustive list of these conventions and notations is provided here for convenience. Some of the conventions and notations herein include: (I) represents spin for a nucleus; ($H_Q$) represents a Hamiltonian Operator; $(Q)^m$ represents a tensor that involves products of spin operators; (∇E) represents tensors involving the gradients of the electric field at the site of the nucleus; ($E_m$) represents quadrupolar energy levels; (η) represents an asymmetry parameter; (QCC) represents a quadrupolar coupling constant; ($v_H$, $v_L$) represent resonant frequencies; and (m) represents a spin quantum number. Note that other variables and quantities do appear herein. Accordingly, some of these other variable and quantities are defined elsewhere in this disclosure. Further, the foregoing list should be taken in the context of the disclosure where such conventions and notations appear, and any perceived conflicting definitions should be treated as such. As such, this foregoing list is provided for convenience alone.

Quadrupolar Hamiltonian Operator ($H_Q$). When a nucleus has a magnetic spin quantum number greater than (½), quantum mechanics requires that the nucleus have an electric quadrupole moment in addition to a magnetic moment. The electric quadrupole moment interacts with the electric field gradient at the site of the nucleus and generates splittings in the energy spectrum of the nucleus. The Hamiltonian Operator ($H_Q$) for this interaction is expressed as:

$$H_Q = \sum_{m=-l}^{l} Q_2^m (\nabla E)_2^{-m}, \quad (1);$$

where $Q_2^m$ represents second order tensors that involve products of the spin operators, and $(\nabla E)_2^m$ represents second order tensors involving derivatives (gradients) of the electric field (E) at the site of the nucleus.

Finding Eigenvalues for this interaction is therefore daunting, at least in the general case. However, some simplification may be applied when transforming the Hamiltonian operator ($H_Q$) to a set of principle axes. Simplification calls for realizing that the electric field gradient tensor (=E) be symmetric and traceless. When a Laplace transformation is performed, the quadrupolar Hamiltonian operator ($H_Q$) in the coordinate system, for the principle axis becomes:

$$H_Q = \frac{e^2 Qq}{4I(2I-1)}\left[(3I_z^2 - I^2) + \frac{\eta}{2}(I_+^2 + I_-^2)\right]. \quad (2)$$

where ($e^2Qq$) represents the quadrupole coupling constant, QCC or $Q_{CC}$; and ($\eta$) represents an asymmetry parameter; and (I) represents the spin for the nuclei. The asymmetry parameter ($\eta$) varies from zero (0) to one (1). When the asymmetry parameter ($\eta$) is zero, there is axial symmetry around a principal axis in the coordinate system (the z-axis).

The principal axes are a function of the lattice properties of the crystal in which the quadrupolar nucleus resides. These axes will vary in orientation if the nuclei reside in several different sites of a unit cell. In a single crystal sample, each unique lattice site will have a different orientation with regard to the applied RF magnetic field. This is important as the sensitivity of the NQR measurement is dependent upon this orientation. If the sample is polycrystalline, one must average the Hamiltonian Operator ($H_Q$) over all orientations of the principal axes.

Axial Symmetric Case. In the axially symmetric case, where the asymmetry parameter ($\eta$)=0, and the Hamiltonian Operator ($H_Q$) is diagonal, the energy levels ($E_m$) are given by Eq. (3):

$$E_m = A[3m^2 - I(I+1)], \quad (3)$$

where $$A = \frac{e^2 Qq}{4I(2I-1)}. \quad (4)$$

The energy levels ($E_m$) are degenerate for ±m. In units of A, the energy levels ($E_m$) are 10, −2, and −8 for m=±5/2, ±3/2, and ±1/2 respectively. In FIG. 1, the quadrupolar energy levels ($E_m$) are, shown for zero magnetic field for spin (I=5/2). The electric field gradient ($\nabla E$) at the site of the nucleus is q. The spin quantum numbers, m, are shown at the right.

Transitions between the quadrupolar energy levels ($E_m$) can occur for axial symmetry at (2I−1)/2 unique frequencies. In the case where the spin (I) is (5/2), the number of frequencies is two (2) as shown in FIG. 1. The transitional frequencies are given by Eq. (5):

$$\hbar\omega_{\pm m} = 3A(2|m|+1), \quad (5)$$

where m represents the quantum number of the lower energy state. For the example where the spin (I) is (5/2), the transitional frequencies in units of A/$\hbar$ are 6 and 12 for the ±1/2 to ±3/2, and the ±3/2 to ±5/2 transitions, respectively.

Nonsymmetric Case. In the absence of a static magnetic field and when the asymmetry parameter ($\eta$)≠0, the Hamiltonian operator ($H_Q$) has off-diagonal elements that mix the state of the spin quantum numbers, m, with m±2. Thus, the secular equation must be solved to determine both the eigenvectors and eigenvalues. This amounts to solving the determinant equation provided in Eq. (6) for E:

$$|H_Q - 1E| = 0 \quad (6);$$

which amounts to solving a 2I+1 order polynomial. However, because mixing occurs only between state m and m±2 the Hamiltonian operator ($H_Q$) can be divided into two submatrices of dimension (2I+1)/2. For spin 5/2, the secular equation becomes third order, and is represented shown in Eq. (7):

$$\left(\frac{E}{2A}\right)^3 - 21(1+\eta^2/3)\left(\frac{E}{2A}\right) - 20(1-\eta^2) = 0. \quad (7)$$

Figure 2:
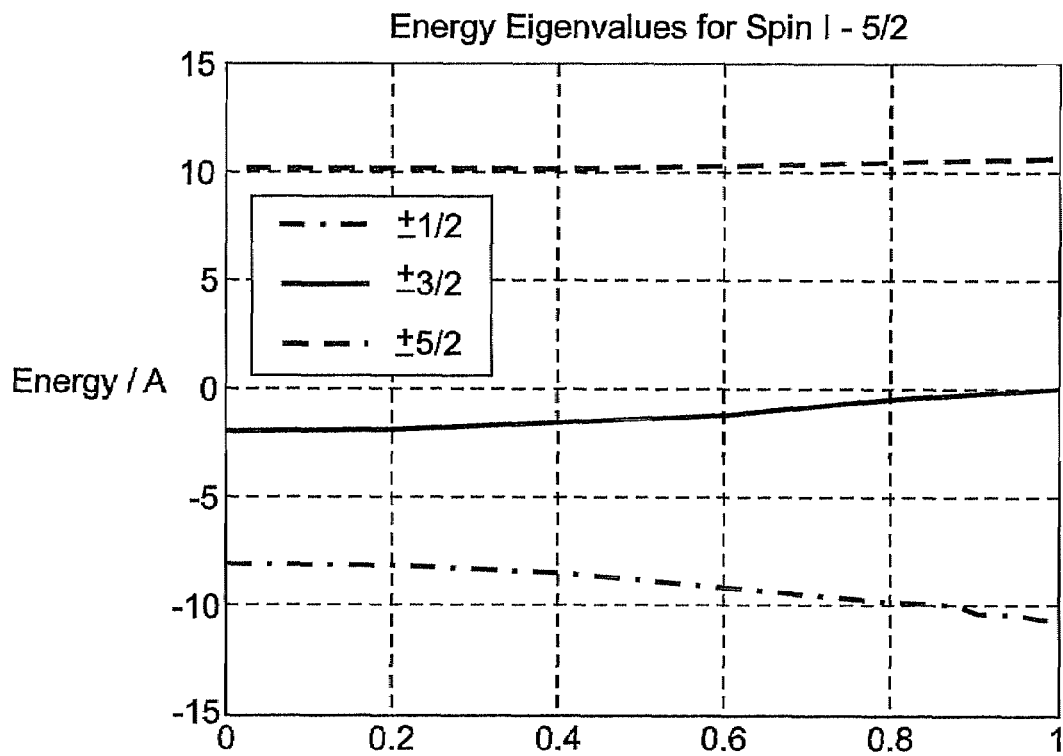
FIG. 2 is a graph depicting Eigenvalues for a I=5/2 quadrupolar Hamiltonian operator as a function of an asymmetry parameter, η.

In FIG. 2, the Eigenvalues for the I=5/2 quadrupolar Hamiltonian Operator ($H_Q$) are plotted as a function of the asymmetry parameter ($\eta$). The quantities graphed correspond to the spin states at $\eta$=0. For $\eta$>0, the eigenvectors contains admixtures of the other spin states but remain substantially in the spin state indicated. In the case where the spin (I) is (5/2), the eigenvectors have two distinct transition energies in the axisymmetric case. This is reduced to a single resonance when there is no symmetry. The resonant frequencies, $v_H$ and $v_L$, are given by Eq. (8):

$$v_H = \frac{mQ_{cc}}{2}(3\cos\zeta - \sqrt{3}\sin\zeta) \quad (8)$$

$$v_L = \sqrt{3}\, mQ_{cc}\sin\zeta$$

$$m = \frac{1}{10}\sqrt{7(1+\eta^2/3)}$$

$$\cos 3\zeta = \frac{10(1-\eta^2)}{[7(1+\eta^2/3)]^{3/2}}.$$

Effect of Strong RF Magnetic Field. When an RF magnetic field is applied to this system, it can create transitions between energy levels with Δm=±1. In the axial symmetric case, the effect of a pulse along the x-principal axis is given by (Das and Hahn 1958; Petersen 1975; Edwards 2005) as provided in Eq. (9):

$$\langle I_x(t)\rangle = -\frac{\lambda_-}{2I+1}\frac{\hbar\omega_m}{kT}\sin(\lambda_-\omega_1\tau_p)\sin\omega_m t, \quad (9)$$

$$\langle I_y(t)\rangle \equiv \langle I_z(t)\rangle \equiv 0.$$

Here $\lambda$ represents the constant defined by the lowering operator, as shown in Eq. (10):

$$I_\pm|I,m\rangle = \lambda_\pm|I,m\pm 1\rangle;$$

$$\lambda_\pm = \sqrt{I(I+1) - m(m\pm 1)}; \quad (10)$$

where $\omega_m$ represents the transition frequency; m represents the quantum number of the highest energy level; $\tau_p$ represents the pulse width; and $\omega_1 = \gamma B_1$ represents the measure of the amplitude of the RF magnetic field.

Das and Hahn (Das and Hahn 1958) have shown that spin echoes occur after two pulses. They show that for two identical pulses, Eq. (11) is realized:

$$\langle I_x(TE)\rangle \propto \sin\xi \sin^2\xi/2$$

$$\xi = \lambda_-\omega_1\tau_p. \quad (11)$$

Figure 3:
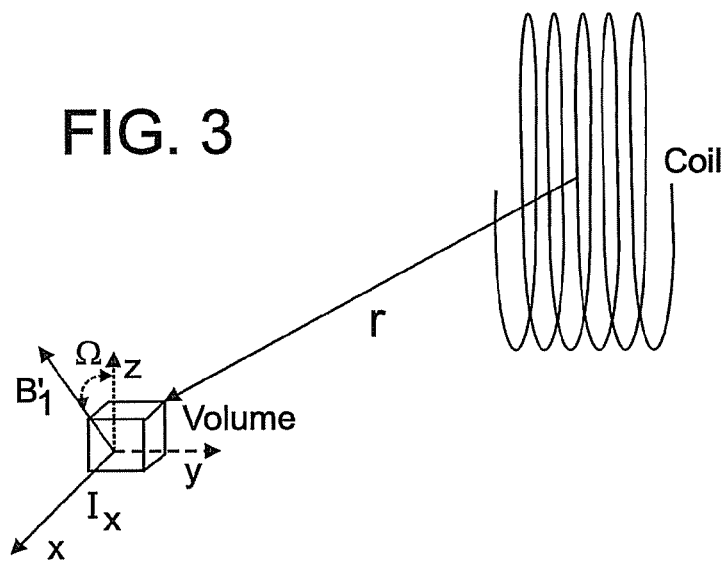
FIG. 3 depicts an orientation of the radiofrequency (RF) magnetic field and the x-component of the induced magnetization.

Marino (Marino and Klainer 1977; Marino, Wenk et al. 1980) have also shown that multiple pulse sequences similar to the CPMG will produce multiple echoes in quadrupolar systems. Finally, an expression for the induced EMF in an RF coil can be derived. The signal dS(r,t) is given by the reciprocity theorem, provided in Eq. (12):

$$dS(r, t) = -\frac{\partial}{\partial t}(B'(r)_1 \cdot dm(r, t)), \quad (12)$$

where $B'_1$ represents the magnetic field when a unit current is applied to the coil and dm represents the magnetic moment in a volume element dV. At a given location in the RF field of the coil, the z-principle axis is oriented with a direction $\Omega$ with respect to the RF field as shown in FIG. 3, if a single coil system is used. In such case, $©B'(r)_1 \exists dm(r,t)^{TM}{}_\Omega$ is defined by Eq. (13):

$$\langle B'_1(r) \cdot dm \rangle_\Omega = \gamma \hbar B'_1(r) \langle \sin\Omega \langle I_x(t) \rangle \rangle_\Omega \quad (13)$$

$$= \gamma \hbar B'_1(r) \left( \frac{1}{4\pi} \int_0^{2\pi} d\phi \int_0^\pi d\Omega \sin\Omega \langle I_x(t) \rangle \right)$$

Applying Eq. (9) to the reciprocity theorem, one can integrate over the direction $\Omega$, and arrive at an expression for the signal from an elemental volume, dV, as provided in Eq. (14):

$$dS = \frac{\pi}{2(2I+1)} \lambda_- \gamma B'_1(r) \frac{\hbar^2 \omega^2}{kT} J_1(\lambda_- \gamma B'_1(r) I_p \tau_p) N dV. \quad (14)$$

where $I_p$ represents the current in the coil during the pulse.

Referring to FIG. 3, illustration of the orientation of the RF magnetic field and the x-component of the induced magnetization is provided. Within the volume element, the principal crystal axes are arbitrarily oriented. The RF magnetic field, $B_1$, makes an angle, $\theta$, with $I_x$. Note that in FIG. 3, a coordinate system is depicted. The coordinate system includes a z-axis (also referred to as the principal axis), a y-axis and a x-axis.

The signal from an elemental volume for an NMR experiment can be computed as well. When the RF and static field are perpendicular, the differential signal $dS_{NMR}$ may be approximated by Eq. (15):

$$dS_{NMR} \approx (\omega B'_1(r)) \left( \frac{\gamma^2 \hbar^2 I(I+1)}{3kT} B \right) N dV. \quad (15)$$

Using Eq. (15), the ratio of the signal from an NMR experiment using an equal number of protons and an NQR experiment at the same resonant frequency under optimum excitation conditions can be computed. The ratio (R) may be approximated by Eq. (16):

$$R \approx 3.66 \frac{\lambda_-}{2I+1} \frac{\gamma}{\gamma_p} c, \quad (16);$$

where c represents natural abundance of the isotope of interest. Various values for the ratio (R) have been tabulated and are presented in Table 1. One skilled in the art will recognize that given the optimum excitation conditions, the NQR for $^{23}$Na and $^{27}$Al have signal amplitudes that are the same order of magnitude when compared to the signal from an equal number of protons. This includes the reduction of signal caused by the natural abundance of the isotopes in question. It should be noted that the relative sensitivity increases when the lower frequency transitions are considered.

TABLE 1

Ratio of NQR signal to NMR signal in an elemental volume for optimum excitation

| Isotope | Spin (I) | Transition | Ratio (R) |
|---|---|---|---|
| $^{23}$Na | 3/2 | 3/2 to 1/2 | 0.419 |
| $^{25}$Mg | 5/2 | 5/2 to 3/2 | 0.00847 |
|  |  | 3/2 to 1/2 | 0.0107 |
| $^{27}$Al | 5/2 | 5/2 to 3/2 | 0.356 |
|  |  | 3/2 to 1/2 | 0.450 |
| $^{39}$K | 3/2 | 3/2 to 1/2 | 0.0689 |

III. Evaluation of Mineralogy. This section considers aspects of use of NQR techniques to identify rock minerals in reservoir rock. One particular aim is to identify and quantify clay minerals in the reservoir rock. However there are other minerals that may be of interest and those should be investigated as well.

TABLE 2

Elemental composition of sedimentary rocks (in number percent (mole/mole))

| Element | Isotope | Abundance (%) | Sandstones (%) | Shales (%) | Carbonates (%) |
|---|---|---|---|---|---|
| Oxygen | $^{17}$O | 0.037 | 65.6 (0.024) | 65.7 (0.024) | 61.2 (0.0230) |
| Aluminum | $^{27}$Al | 100 | 3.18 (3.18) | 5.86 (5.86) | 0.96 (0.96) |
| Calcium | $^{43}$Ca | 0.145 | 2.14 (0.003) | 2.63 (0.004) | 13.5 (0.02) |
| Potassium | $^{39}$K | 93.1 | 0.99 (0.92) | 1.45 (1.35) | 0.08 (0.08) |
| Magnesium | $^{25}$Mg | 10.13 | 0.92 (0.094) | 1.59 (0.16) | 3.59 (0.36) |
| Sodium | $^{23}$Na | 100 | 0.42 (0.42) | 0.57 (0.57) | 0.05 (0.052) |

In Table 2, the number percentage of the quadrupolar nuclear species for the element is shown in parentheses. The data used to construct the table were taken from Huang. (Huang 1962). This data was in the form of weight percent and was used to calculate the number percent (mole element/mole mineral) of the various elements shown in parentheses. The number percent of the most abundant quadrupolar nuclear species for that element is shown in parentheses. It is these last numbers that are important to the development of a NQR logging tool.

Given Eq. (16), and the number percent of the quadrupolar nuclei shown in Table 2, one skilled in the art can conclude that $^{27}$Al is probably detectable in sandstones, shales and carbonates; $^{39}$K might be detectable in sandstones and shales as well; and although abundance is less the ½ of 1%, $^{25}$Mg might be barely detectable in carbonates while $^{23}$Na should be detectable in sandstones and shales. These estimations are considered reasonable based on the knowledge that NMR logging tools are able to detect fluids in a rock with a porosity of 1%. However given that the signal detected will come from entire volume of the coil and not just a thin slice or other limited volume of the rock, this assessment may be unduly conservative. Accordingly, a more accurate assessment is considered later herein.

Minerals in Reservoir Rocks Containing Aluminum. Almost all types of minerals can be found in sedimentary rocks because they are created by both mechanical and chemical processes The mineral detritus generated from the physical and chemical weathering of igneous or metamorphic rocks are subject to mechanical transport and chemical dissolution. Those minerals which survive transport and others that are transformed into other minerals during chemical weathering are the most stable and abundant minerals found in sedimentary rocks. The common and abundant minerals in sedimentary rocks are: quartz, feldspar, micas, calcite, dolomite, and clay minerals. (Huang 1962).

These minerals can generally be classified into two groups: silicates and carbonates. The silicates include quartz, feldspar, micas, and clay minerals. The basic structures are composed of Si—O tetrahedra, mainly as $SiO_4$. The silicon ions are bonded to oxygen as $SiO_4$. These can be organized in chains, sheets, or composite structures, such as feldspars and quartz, while sheet structures (two-dimensional (2D)) are evident in micas and clay minerals.

When aluminum is present in the mineral, it generally occupies either a tetrahedral or an octahedral site. Iron and Magnesium can also substitute into the octahedral site. Other cations composing the structure tend to occupy the interstitial spaces between tetrahedral, octahedral sites between sheets of tetrahedral or octahedral sites between double layers of tetrahedral depending on their size and charge. An example is depicted in FIG. 4.

Figure 4:
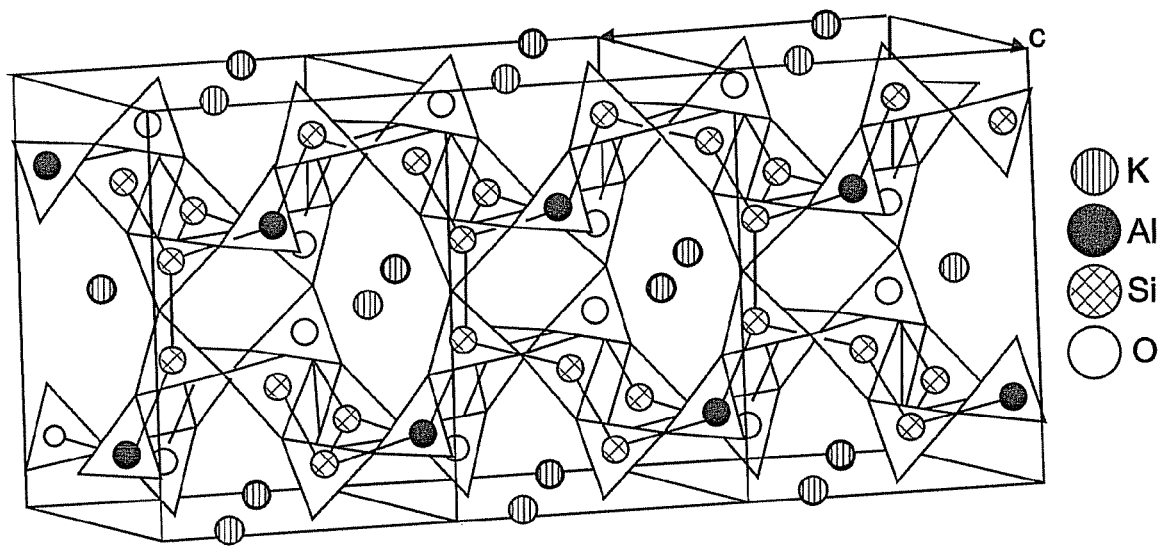
FIG. 4 depicts a crystal structure of potassium feldspar ($KalSi_3O_8$)

In FIG. 4, a crystal structure of potassium feldspar ($KAlSi_3O_8$) is depicted. Note that the aluminum occupies tetrahedral sites and the potassium is in the interstitial spaces between the tetrahedral of $AlO_4$ and $SiO_4$.

Feldspar. Feldspars are the second most abundant mineral group in arenaceous (sand-like) sediments. They are classified not only by chemical composition, but also by their structure. Most feldspars are classified chemically from the ternary system of $NaAlSi_3O_8$—$KAlSi_3O_8$—$CaAl_2Si_2O_8$. These are referred to as sodic feldspar, potassic feldspar and calcic feldspar.

Feldspars are composed of linked tetrahedra of $AlO_4$ and $SiO_4$. The sodium, potassium, and calcium ions reside in the interstitial spaces between the tetrahedra. An illustration of the crystal lattice is shown in FIG. 4. The symmetry of the $AlO_4$ requires that the electric field gradient caused by the oxygen atoms will be zero at the aluminum site. However, the symmetry of the unit cell breaks the symmetry of the lattice site and some electric field gradient will exist at the aluminum sites. In addition, the symmetry of the alkali ion sites will permit the existence of the electric field gradients there as well.

Figure 5:
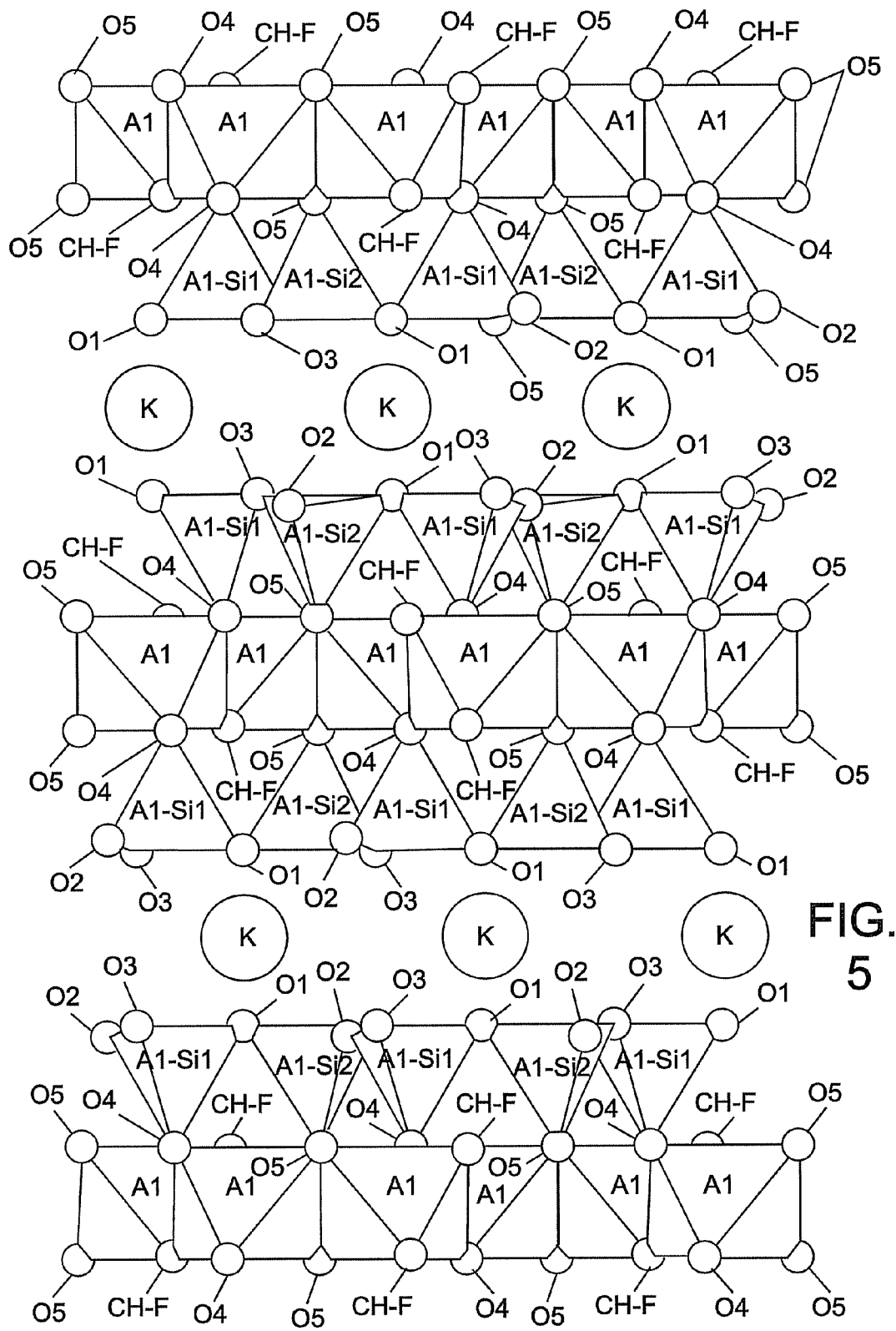
FIG. 5 depicts a crystal structure of muscovite.

Mica. Mica crystal structure contains planes of tetrahedra of either $AlO_4$ or $SiO_4$, connected to each other by octahedral sites with aluminum or some other metal ion. They may typically contain potassium (Muscovite), magnesium, (Lepidolite and Phlogpite) as well as other metals. The structure is such that any quadrupolar nuclei should experience field gradients at their lattice sites. The crystal structure of Muscovite is shown in FIG. 5. In FIG. 5, aluminum ions occupy octahedral sites between layers of $SiO_4$ and $AlO_4$. Potassium ions occupy the space between the double layers.

Clay Minerals. "Clay" denotes a mineral group and as such encompasses a number of different mineral species. They are classified as phyllosilicates. The minerals are formed of layers of Si—O tetrahedra interspersed with layers of aluminum or some substitutional ion in the octahedral layers.

The silica layer is comprised of layers silicon atoms tetrahedrally coordinated to four oxygen atoms. The basal planes of six tetrahedra are linked together in a hexagon pattern such that two oxygen atoms from each of the tetrahedra are shared with all the tetrahedral having the same orientation perpendicular to the plane. The octahedral layer is comprised of OH groups of oxygen ions in octahedral coordination about $Al^{3+}$, $Mg^{2+}$, or other cation. When aluminum is present, the structure is known as gibbsite ($Al(OH)_3$). In Gibbsite, one third of the octahedral sites are empty and the layer is considered dioctahedral. When all of the octahedral sites are occupied the layer is considered to be trioctahedral.

The octahedral and tetrahedral layers are combined by substituting tetrahedral oxygen structures that are not in the basal plane of the tetrahedral layer for the octahedral OH groups. If only one octahedral layer and one tetrahedral layer are combined, this is known as a 1:1 clay and is typical of Kaolinite. A Smectite, such as Montmorillonite, is formed when two tetrahedral layers are combined with a single octahedral layer. It is known as a 2:1 clay. Chlorite is a 2:1:1 clay. In this structure layers of the 2:1 structure are interleaved with an aluminum octahedral layer.

Figure 6A:
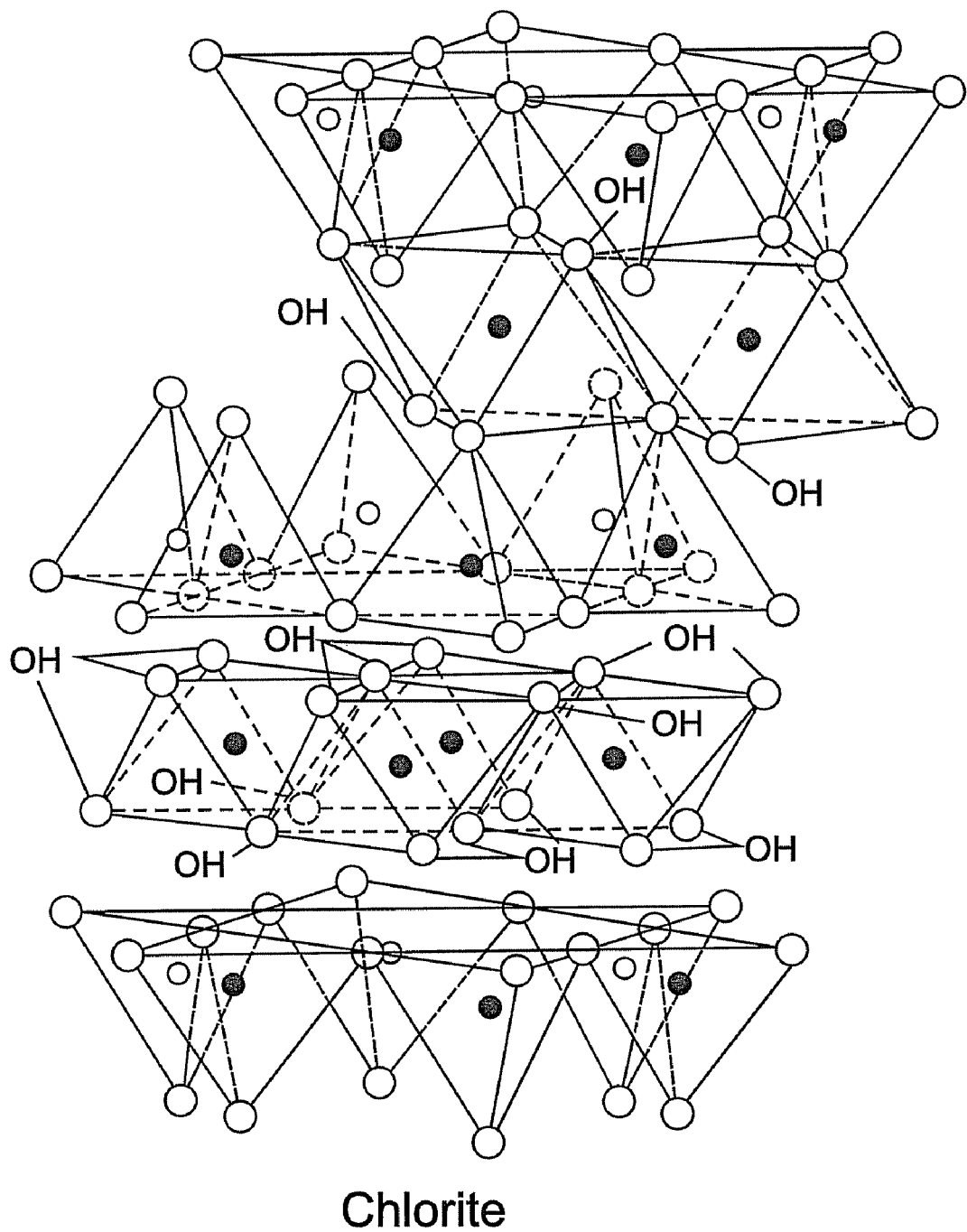
FIG. 6 depicts typical clay mineral structures.
Figure 6C:
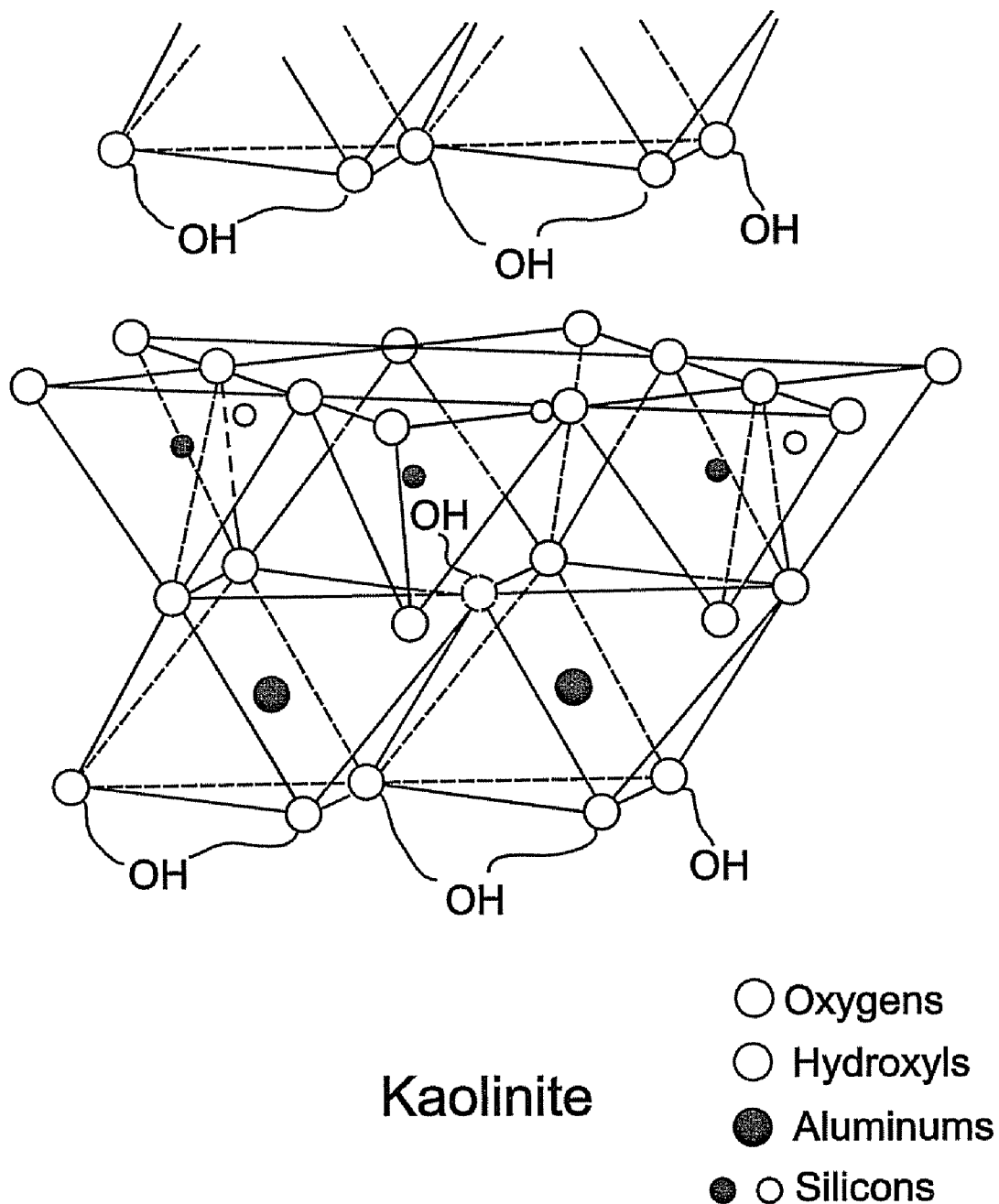

Various cations can be substituted for $Al^{3+}$ in the octahedral layers to form different species of clays. In addition, $Al^{3+}$ can be substituted for the $Si^{4+}$ in the tetrahedral layer. Each of these types of substitutions may form a different type of clay. Examples of the structures are shown in FIG. 6, which depicts typical clay mineral structures.

IV. NMR and NQR Properties of Minerals. The foregoing section summarizes the crystal structure and composition of minerals commonly found in a reservoir where petroleum products may reside. The quadrupolar nuclei commonly found in these minerals are shown in Table 3. Given the relative abundance and the magnitude of their quadrupolar moment, it is considered that these are principle candidates for NQR logging. Of these isotopes, $^{27}$Al is predominates as it is in many of the minerals of interest in the reservoir including feldspars, micas and clay minerals (as discussed above).

TABLE 3

Partial list of NQR active isotopes in typical reservoir minerals

| Isotope | Spin (I) | % Abundance Elemental (% Earth's Crust) | Quadrupole Moment ($10^{28}$ Q/m$^2$) |
| --- | --- | --- | --- |
| $^{23}$Na | 3/2 | 100 (2.1) | 0.1 |
| $^{25}$Mg | 5/2 | 10.1 (0.25) | 0.22 |
| $^{27}$Al | 5/2 | 100 (6.3) | 0.15 |

When aluminum is present in minerals, it is either tetrahedrally coordinated or octaherally coordinated. Both of these configurations have sufficient symmetry to generate no electric field gradients from the aluminum nearest neighbors, but more distant neighbors will generate electric field gradients (EFGs). In addition, in some of the crystal configurations, the aluminum nearest neighbors may be different ions such as an $OH^-$ or an $O^{2-}$. When this occurs, EFGs will also be generated.

FIG. 7 shows quadrupole properties for selected minerals. The data provided primarily includes $^{27}Al$ properties but also contains $^{23}Na$ and $^{25}Mg$ entries as well. Some entries include estimates of the quadrupole coupling constant, $Q_{CC}$, and the asymmetry parameter, $\eta$. The data was derived from NMR experiments on single crystals. NMR experiments on polycrystalline samples are usually of the magic angle spinning (MAS) variety and report only the second order quadrupole effect (SOQE), given by Eq. (17):

$$SOQE = Q_{CC}\sqrt{1+\eta^2/3}. \tag{17}$$

Given estimates for the quadrupole coupling constant, $Q_{CC}$, and the asymmetry parameter, $\eta$, exact NQR frequencies can be calculated as shown in Eq. (8). When only the second order quadrupole effect (SOQE) is reported, a range for the NQR frequencies is given.

Different crystal sites will, in general, have different resonant frequencies because the EFGs will be different. Thus, the data in FIG. 7 may report different values for the quadrupole coupling constant, $Q_{CC}$, and the asymmetry parameter, $\eta$ for each lattice site. For example, the neosilicate Kyanite has four different tetrahedral lattice sites in which aluminum may reside. This will result in four different frequencies for the 5/2 to 3/2 transition as well as the 3/2 to 1/2 transition. The site symmetry column indicates the symmetry of the lattice site, if known. The value four indicates a tetrahedral site while six indicates an octahedral site.

The NQR frequencies of phyllosilicates for the 5/2 to 3/2 transition could range from 0.321 to 1.890 MHz as computed from the second order quadrupole effect SOQE. However, the range is much smaller when the quadrupole coupling constant, $Q_{CC}$, and the asymmetry parameter, $\eta$, are used in Eq. (8). In this case, the range is 0.768 to 1.052 MHz. Specifically kaolinite is estimated to have 986 kHz and 768 kHz for the two octahedral aluminum lattice sites.

In FIG. 7, most properties are estimated from NMR studies of single and polycrystalline samples. Polycrystalline samples will only report the second order quadrupole effect SOQE, the second order quadrupole effect and not separately estimate the quadrupole coupling constant, $Q_{CC}$, and the asymmetry parameter, $\eta$. Thus only a range for the quadrupole frequencies is available.

The NQR frequencies for the 3/2 to 1/2 transition have a smaller and lower range. When computed from the second order quadrupole effect SOQE, the range is 0.210 to 1.443 MHz. The range narrows considerably to 572 to 750 kHz when for the quadrupole coupling constant, $Q_{CC}$, and the asymmetry parameter, $\eta$ are used. The 3/2 to 1/2 transitions for both of the octahedral sites are almost identical in Kaolinite, and are 0.742 kHz and 0.750 kHz because the asymmetry parameters differ between the sites.

Figure 8:
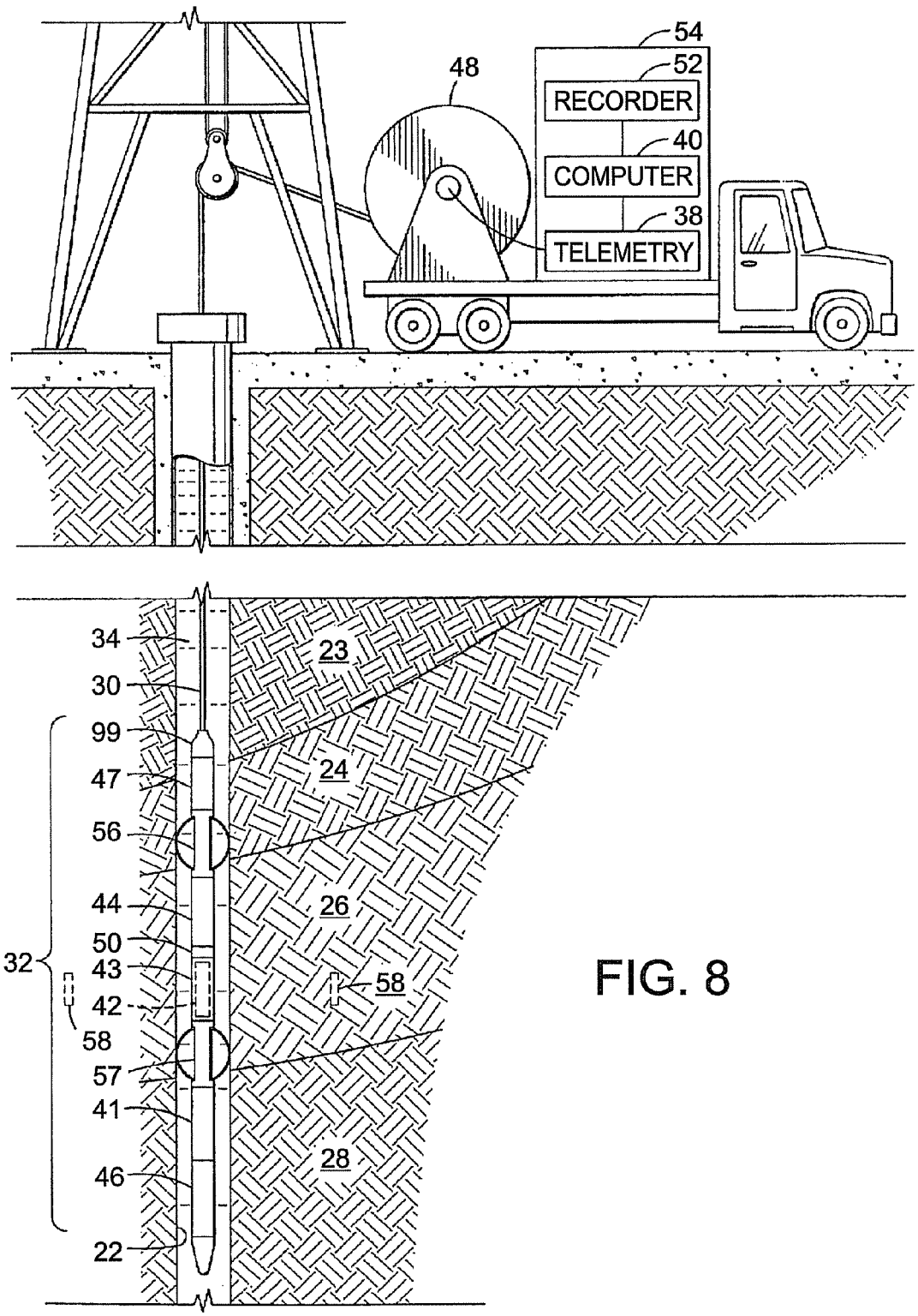
FIG. 8 depicts an exemplary deployment of an NQR instrument.

V. Logging Device. Referring to FIG. 8, aspects of a wellbore and logging instrument are shown. In FIG. 11 a well logging apparatus is disposed in a wellbore 22 penetrating earth formations 23, 24, 26, 28 for making measurements of properties of the earth formations 23, 24, 26, 28. The wellbore 22 in FIG. 8 is typically filled with a fluid 34 known in the art as "drilling mud." A "sensitive volume," shown generally at 58 and having a generally cylindrical shape close to the wellbore, is disposed in one of the earth formations, shown at 26. The sensitive volume 58 includes a predetermined portion of the earth formations 26 in which NQR measurements are made.

In typical embodiments, the sensitive volume 58 includes materials such as would be found within a wellbore 22 including a mixture of liquids including water, (including fresh water and salt water), drilling fluid, minerals, clay, mud, oil and formation fluids that are indigenous to the formations 23, 24, 26, 28, or introduced therein. The NQR measurements may be used to determine a variety of formation properties and other aspects of interest. For example, aspects of mineralogy may be determined or surmised as discussed above.

Exemplary minerals for typing include at least one of detrital minerals comprising $SiO_2$, $Ca_2CO_3$, $Mn_2O_3$ and secondary minerals comprising at least one of a type of clay mineral and a type of evaporate mineral.

The magnitude of the measured internal gradient is dependent on other factors as well. For example, the internal gradient is affected by the curvature of the interface between pore fluid and the rock matrix surface. Thus, the internal gradient is also related to pore geometry. More specifically, for identical minerals, the smaller the pores, the larger the internal gradient. This may provide for certain determinations. For example, for carbonate rocks, the internal gradient may only be significant in the intragranualar pores, and thus may be helpful for surveys of the intragranualar pores.

Many sandstone formation rocks contain certain amount of clay minerals. The distribution of clay minerals may affect the pore geometry significantly. Therefore, the internal gradient is significantly larger for dispersed clay minerals than for structural clay distributions. This is because the former introduces a great amount of surface area interfacing with pore fluid and increases curvature on the interfaces. Thus, if the amount of clay is determined by NQR clay-volumetric measurements or other mineral-sensitive measurements, one will be able to use the internal gradient estimates to predict the clay distributions.

Referring still to FIG. 8, a string of logging tools 32, which can include an NQR apparatus according to the present invention, is typically lowered into the wellbore 22 by a means of an armored electrical cable 30. The cable 30 can be spooled and unspooled from a winch or drum 48. The tool string 32 can be electrically connected to surface equipment 54 by an insulated electrical conductor (not shown separately in FIG. 8) forming part of the cable 30. The surface equipment 54 can include one part of a telemetry system 38 for communicating control signals and data to the tool string 32 and computer 40. The computer may also include a data recorder 52 for recording measurements made by the apparatus and transmitted to the surface equipment 54. Typically, the computer includes a variety of input/output devices and other supporting devices to enhance the operation of the apparatus and estimations performed by use thereof.

An NQR probe 42 can be included in the tool string 32. The tool string 32 is typically centered within the wellbore 22 by means of a top centralizer 56 and a bottom centralizer 57 attached to the tool string 32 at axially spaced apart locations. The centralizers 56, 57 can be of types known in the art such as bowsprings.

Circuitry for operating the NQR probe 42 can be located within an NQR electronics cartridge 44. The circuitry can be connected to the NQR probe 42 through a connector 50. The NQR probe 42 is typically located within a protective housing 43 which is designed to exclude the drilling mud 34 from the interior of the probe 42. The function of the probe 42 will be further explained.

In typical embodiments, the NQR probe 42 calls for modifications to a traditional nuclear magnetic resonance (NMR) logging probe. A commercially available example of an NMR logging probe is the MREX™ logging instrument available from Baker Hughes, Incorporated of Houston Tex.

For further background, other aspects of the related NMR probe are provided in U.S. Pat. No. 5,712,566, entitled "Nuclear Magnetic Resonance Apparatus and Method," issued Jan. 27, 1998 to Taicher et al., and U.S. Pat. No. 4,710,713, also issued to Taicher et al, with certain aspects of both patents being incorporated herein by reference. It should be recognized that these embodiments are directed to NMR tools and are exemplary only. That is, these embodiments are not specifically directed to NQR probes and not to be construed as inconsistent with or limiting of the teachings herein.

As examples of differences between NMR and NQR probes, it is recognized that NQR probes do not call for magnetization. That is, as NQR surveys are performed in a "zero field," magnets used for inducing magnetic fields are not required. In short, the NQR probe typically includes apparatus as necessary for generating a radio-frequency (RF) magnetic field as well as components for receiving and interpreting the RF magnetic field.

The NQR probe 42 is typically operated within a certain frequency range. The reason for this is that the NQR frequencies for clays generally are in the range of 200 kHz to 2 MHz. However, it is recognized that the NQR probe 42 may be operated within, as an example, a range of about 100 kHz to about 3 MHz (refer to FIG. 7). Actual operating frequencies may depend upon, among other things, properties of minerals of interest.

A 2-d dipole antenna serves to maximize sensitivity of the NQR probe 42 because of its favorable $B_1/I$ ratio. In addition, the radiofrequency (RF) magnetic field scales as $1/r^2$ (which maximizes the penetration of the RF into the formation) and consequently maximizes the sensitive volume 58.

Figure 9:
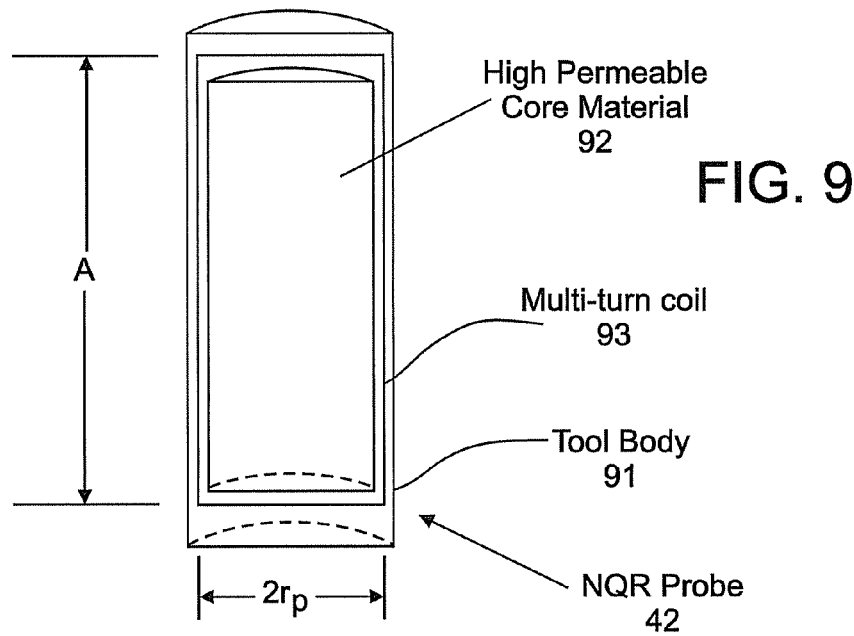
FIG. 9 depicts aspects of an exemplary NQR antenna.

FIG. 9 depicts aspects of an exemplary NQR probe 42. The probe 42 includes a multi-turn coil 93 wound around a cylindrical piece of highly permeable core material 92 that is included within a tool body 91. The length, A, of the probe 42 and the core material 92 is much greater than a respective diameter ($2r_p$) and therefore approximates a 2-dimensional dipole for distances $r_p \ll r \ll A$ into the formations 23, 24, 26, 28. The antenna 90 is connected to hardware similar to that used for pulsed NMR spectrometry and incorporated into the MREX logging tool. In one embodiment, a permeability of about one (1) is used for the material in the core 93. In this embodiment, the probe 42 will have the properties shown in Table 4.

TABLE 4

NQR Probe Properties.

| Property | Value/Expression | Units |
|---|---|---|
| A (coil length) | 0.6 | m |
| $r_p$ (coil radius) | 0.075 | m |
| N (number of turns) | 2 | |
| L (inductance) | 2 | μH |
| Q (quality) | 60 | |
| $B_1/I$ (unit current magnetic field) | $\dfrac{\mu_0 N r_p}{\pi r^2}$ | T/A |
| τ (pulse length) | 100 | μs |

Sensitivity. A signal induced in the coil 93 of the probe 42 is given in Eq. (14). A simplification to Eq. (14) can be made when $A \gg r_p$. The simplification is provided in Eq. (18):

$$B_1'(r) \approx \begin{cases} B_1'(r_0) \dfrac{r_0^2}{r^2} & |z| < A/2 \\ 0 & \text{otherwise.} \end{cases} \quad (18)$$

Integrating over the z-axis and azimuthal angle, the sensitivity (dS) of the NQR one-pulse experiment can be obtained as a function of radius (r) and "flip-angle" $\xi_0$:

$$\frac{dS}{dr} = \frac{\pi V_0}{(2I+1)} \frac{\hbar^2 \omega^2}{kT} \frac{\xi_0}{I_p \tau_p} \frac{1}{r} J_1\left(\xi_0 \frac{r_0^2}{r^2}\right) N. \quad (19)$$

where the "flip-angle" $\xi_0$ at the borehole wall is:

$$\xi_0 = \lambda_- \gamma B_1'(r_0) I_p \tau_p. \quad (20).$$

Figure 10:
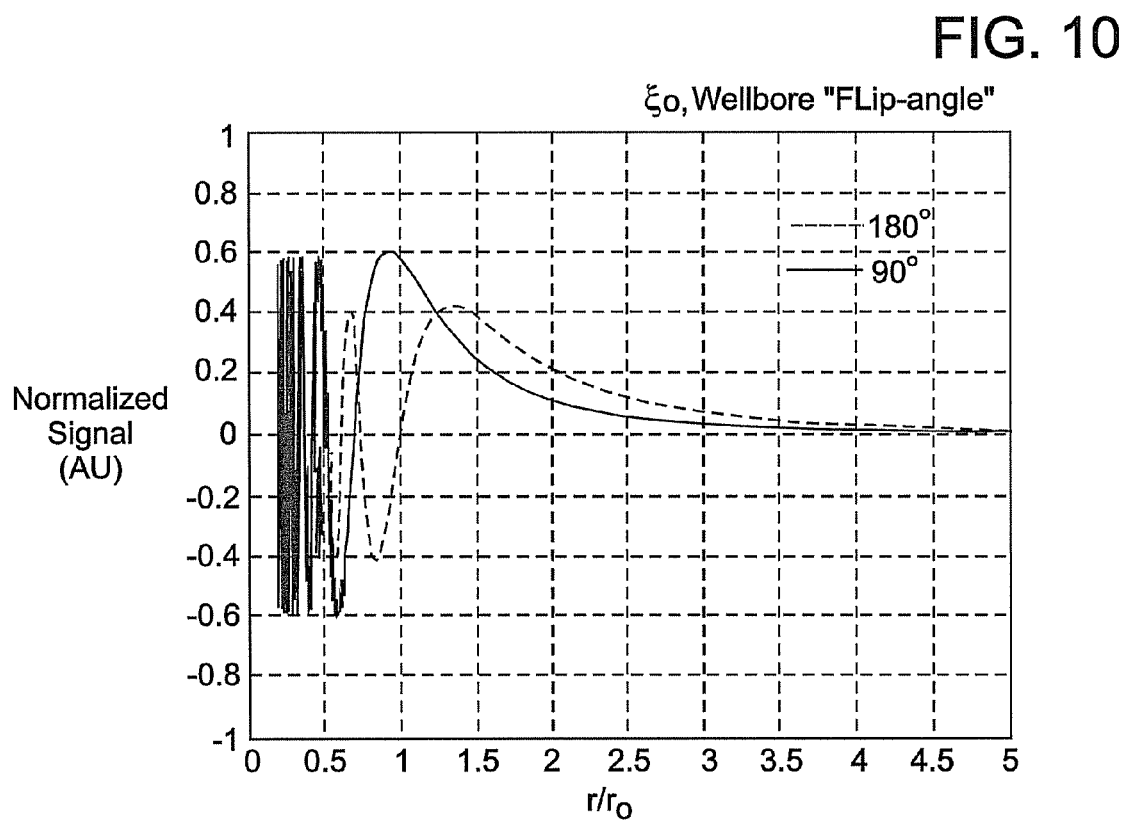
FIG. 10 is a graph plotting a radial sensitivity function for a one-pulse NQR measurement.

Eq. (19) shows that the sensitivity (dS) is an oscillating function of the radius (r). This is shown in FIG. 10, where a function of radial sensitivity is depicted for one-pulse NQR. At small values for the radius (r), the sensitivity (S) rapidly oscillates. These oscillations become more rapid as the radius (r) approaches zero. This is caused by fact that the argument to the Bessel function in Eq. (19) is inversely proportional to the radius squared ($r^2$) and all the zeros of the Bessel functions are mapped into the interval $[0\ r_0 \sqrt{\xi_0/3.8317}]$. In this interval, 3.8317 represents the first zero of Bessel function in Eq. (19). Where the radius (r) is larger than the upper limit of this interval, there are no oscillations. It is important to note that the oscillations will tend to eliminate borehole signal.

Eq. (19) can be integrated analytically. The integration of the radius (r) is over the interval $[r_0\ \infty]$, where $r_0$ is the borehole radius (or at least the radius below which a signal is not desired).

$$\overline{S} = \frac{\pi V_0}{(2I+1)} n \frac{\hbar^2 \omega^2}{kT} \left[ \frac{\xi_0}{I_p \tau_p} \left( J_1(\xi_0) + 2 \sum_{k=1}^{\infty} J_{2k+1}(\xi_0) \right) \right], \quad (21)$$

In FIG. 10, the radial sensitivity function (S) is plotted for one-pulse NQR, as a ratio of the radius (r) to the wellbore radius with two different flip angles $\xi_0$ at the wellbore. For the 180°, $\xi_0$=1.8412, for 90°, $\xi_0$=3.8317.

The normalized signal (the sum from Eq. (21)) is plotted as a function of $\xi_0$ in FIG. 11. It should be noted that in this plot there is a factor of $\xi_0$ outside the sum. When this is included, the normalized signal diverges for large flip angles $\xi_0$. However, the proper limit is to increase the flip angle $\xi_0$ by increasing the current, $I_p$, or the pulse length, $\tau_p$. In either case, $\xi_0/I_p\tau_p$ is fixed and the normalized signal reduces to what is shown in FIG. 11. Also shown are values for the flip angle $\xi_0$ at the borehole radius.

In FIG. 11, the vertical lines represents values of the flip angle $\xi_0$ that correspond to a flip-angles of integer multiples of 90° in an NMR system. As the flip angle $\xi_0$ increases from zero, the signal intensity rises sharply to a local maximum where the flip angle $\xi_0$=3.8317. This maximum represents the flip angle of 180° for an NMR signal. There are then a series of local maxima and minima as the signal slowly approaches in an average way toward its asymptotic value. The local extrema correspond to zeros in the sum from Eq. (19). Each extrema correspond to a flip-angle of integer multiples of 180° for an NMR system. Note that the asymptotic limit for large flip-angles $\xi_0$ is unity.

Noise and SNR. The noise ($N^2$) of the system can be estimated from the Q of the coil 93 and the expression for thermal noise ($N^2$) in a given coil 93:

$$N^2 = 4k_B TR\Delta f \quad (22)$$

where R represents the resistance of the coil 93, T represents the temperature and $\Delta f$ represents the bandwidth of the receiver. NQR resonances in minerals are expected to have line-widths between 10 and 50 kHz. Therefore, the resistance R of the coil 93 is estimated from:

$$Q = \frac{\omega L}{R}. \quad (23)$$

Thus an expression for the electromagnetic frequency (EMF) noise (N) is obtained, and expressed as:

$$N = 2\sqrt{k_B T \omega L \Delta f / Q} \quad (24);$$

where Q varies between 10 and 50 for the typical NMR instrument downhole, and these numbers are applicable here as well. Table 5 shows the estimates for the noise voltage and the SNR of a 100% Kaolinite formation 23, 24, 26, 28. Even in the most unfavorable conditions, the noise voltage is estimated to be 36 nV and when combined with the estimate of the signal from Kaolinite, the SNR is estimated to be about 142. It should be noted that typically in NMR logging, the SNR is less than twenty (20) even after the signal has been averaged as many as sixteen (16) to thirty-two (32) times.

TABLE 5

Noise voltage and signal-to-noise ratio (SNR) for 100% Kaolinite formation

| Coil Quality | $\Delta f$ (kHz) | Noise (nV) | SNR |
|---|---|---|---|
| 10 | 10 | 16 | 318 |
| 50 | 10 | 7.2 | 712 |
| 10 | 50 | 36 | 142 |
| 50 | 50 | 16 | 318 |

Acquisition Schemes. The forgoing discussion of the signal and the SNR has assumed a single one-pulse experiment. Pure NQR has pulse sequences that are analogous the CPMG sequences as well as steady-state free precession (SSFP) sequences. Both of these types of acquisitions can improve the SNR of NQR acquisitions as shown in present techniques for detection of land mines and narcotics.

FIG. 12 provides an exemplary method 120 for performing an NQR evaluation of earth formations 23, 24, 26, 28. The method 120 calls for, in a first step 121, inserting an NQR probe 42 into a wellbore 22. In a second step 122, the probe 42 provides at least one radiofrequency (RF) signal. The RF signal may be pulsed or continuous wave (CW) and may be of multiple frequencies. In a third step 123, RF signals from the formations 23, 24, 26, 28 is acquired. In a fourth step 124, the data are analyzed to determine aspects of formation mineralogy using techniques as are known in the art of NMR analyses.

Alternate Embodiments. The NQR probe 42 previously discussed is a pulsed RF device. However, NQR resonances can also be detected using continuous wave (CW) methodologies. CW methods have the advantage that very little power is used. Typically, pulsed methods have better signal-to-noise ratios the CW methods, but given the estimated SNR of the pulsed device, a CW device could be used and provide for other certain advantages.

As discussed herein, $^{27}$Al is ubiquitous in minerals, occupying octahedral and tetrahedral sites. Each of these sites has a unique electric field gradient so that each site has a unique set of pure NQR resonances. The frequency of these resonances range from a few hundred kilohertz to several megahertz. Estimating the intensity of resonances associated with different minerals is a promising method of estimating the mineral content of the formation.

Using a simple coil 93 having two turns and a simple one pulse sequence, the SNR for a 100% kaolinite formation is at least 140. There a number of ways to improve the SNR through the use of multiple pulse sequences. Thus, using NQR provides a favorable SNR for downhole detection of minerals of interest. In fact, the SNR is much larger than the SNR for a typical NMR logging tool. This arises chiefly from the fact that the excitation volume of the tool includes all of the formation 23, 24, 26, 28, not just a thin annulus, toroid, or hotdog shaped sensitive volume.

In some embodiments, commercially available instrumentation slightly modified to provide for use of NQR technology. For example, the MREX instrument available from Baker Hughes, Incorporated of Houston, Tex. may be modified for implementation of NQR. The NQR frequencies are in the proper range to be excited by the instrumentation. The resulting RF magnetic field strength is in the proper range to excite the full width of the resonances.

It is important to note that the NQR spectrum contains information on more than just elemental composition. The spectrum contains many resonances. There are at least two resonances for $^{27}$Al for every site in a mineral lattice and therefore a set of resonances for every aluminum bearing mineral. Each resonance is likely to be unique because its frequency depends on the characteristics of the specific lattice site and therefore the specific mineral from which the resonance emanates. If the amplitude of a specific resonance is measured, this will provide an estimate of the aluminum content of a specific lattice site in a specific mineral in the formation.

Once simple experiments have provided a more extensive list for $^{27}$Al quadrupole resonances in minerals, it will be possible to obtain more information regarding mineral using NQR as the logging technique.

In-situ stress measurements are made possible by the stress-strain relationship. The electric field gradient at the site of the probe nuclei will change because of the strain produced by either a uniaxial applied stress or uniform stress caused by pressure. This will change the characteristics of the NQR phenomenon and in principle be measurable. Reservoir temperatures may also be measurable because of thermal expansion of the lattice structure.

In support of the teachings herein, various analysis components may be used, including digital and/or an analog systems. The system may have components such as a processor, storage media, memory, input, output, communications link (wired, wireless, pulsed mud, optical or other), user interfaces, software programs, signal processors (digital or analog) and other such components (such as resistors, capacitors, inductors and others) to provide for operation and analyses of the apparatus and methods disclosed herein in any of several manners well-appreciated in the art.

It is considered that these teachings may be, but need not be, implemented in conjunction with a set of computer executable instructions stored on a computer readable medium, including memory (ROMs, RAMs), optical (CD-ROMs), or magnetic (disks, hard drives), or any other type that when executed causes a computer to implement the method of the present invention. These instructions may provide for equipment operation, control, data collection and analysis and other functions deemed relevant by a system designer, owner, user or other such personnel, in addition to the functions described in this disclosure.

Further, various other components may be included and called upon for providing for aspects of the teachings herein. For example, a sample line, sample storage, sample chamber, sample exhaust, pump, piston, power supply (e.g., at least one of a generator, a remote supply and a battery), vacuum supply, pressure supply, refrigeration (i.e., cooling) unit or supply, heating component, motive force (such as a translational force, propulsional force or a rotational force), magnet, electromagnet, sensor, electrode, transmitter, receiver, transceiver, controller, optical unit, electrical unit or electromechanical unit may be included in support of the various aspects discussed herein or in support of other functions beyond this disclosure.

One skilled in the art will recognize that the various components or technologies may provide certain necessary or beneficial functionality or features. Accordingly, these functions and features as may be needed in support of the appended claims and variations thereof, are recognized as being inherently included as a part of the teachings herein and a part of the invention disclosed.

While the invention has been described with reference to exemplary embodiments, it will be understood by those skilled in the art that various changes may be made and equivalents may be substituted for elements thereof without departing from the scope of the invention. In addition, many modifications will be appreciated by those skilled in the art to adapt a particular instrument, situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. An instrument for investigating properties of an earth formation, the instrument comprising:
   a body housing a nuclear quadrupole resonance (NQR) probe, the probe consisting essentially of at least one coil adapted for at least one of providing a pulsed radiofrequency signal configured to detect an earth formation layer and receiving a return radiofrequency signal from the earth formation without inducing a polarizing magnetic field and an electronics coupling, the body being adapted for insertion into a wellbore within the earth formation.

2. The instrument as in claim 1, wherein the at least one coil comprises a multi-turn coil.

3. The instrument as in claim 1, wherein the coil is wound around or adjacent to core material.

4. The instrument as in claim 3, wherein the core material comprises a permeability of about one.

5. The instrument as in claim 1, wherein the electronics coupling provides a connection to spectrometry electronics.

6. The instrument as in claim 1, wherein dimensions of the NQR probe are selected to approximate a two-dimensional dipole antenna.

7. The instrument as in claim 1, wherein a length of the NQR probe is much greater that a diameter of the NQR probe.

8. A method for investigating properties of an earth formation, the method comprising:
   selecting an instrument comprising a body housing a nuclear quadrupole resonance (NQR) probe, the probe consisting essentially of at least one coil adapted for at least one of providing and receiving a radiofrequency signal without inducing a polarizing magnetic field and an electronics coupling, the body being adapted for insertion into a wellbore within the earth formation;
   disposing the instrument within a wellbore;
   directing a pulsed radio frequency (RF) signal into the formation without inducing a polarizing magnetic field, the RF signal configured to detect an earth formation layer;
   acquiring a NQR signal from the formation; and
   interpreting the NQR signal to determine the properties of the earth formation layer.

9. The method as in claim 8, wherein the radiofrequency comprises a frequency of between about one hundred kilohertz to about three megahertz.

10. The method as in claim 8, wherein directing comprises selecting a radiofrequency according to mineralogy of the formation.

11. The method as in claim 8, wherein selecting comprises selecting the NQR probe for at least one of maximizing a penetration of the RF signal into the formation and maximizing a sensitive volume in the formation.

12. The method as in claim 8, wherein directing comprises increasing at least one of a current and a pulse length of the RF signal to increase a flip angle $\xi_0$.

13. The method as in claim 8, wherein determining the properties comprises determining an identity of a mineral in the formation.

14. The method as in claim 13, wherein the mineral comprises at least one of chlorite, smectite, kaolinite, muscovite, feldspar, and a mineral that bears at least one of hydrogen, carbon, oxygen, nitrogen, arsenic, copper, boron, aluminum, chlorine, sodium, manganese, magnesium, potassium, silicon and calcium.

15. A computer program product stored on machine readable media comprising machine executable instructions for investigating properties of an earth formation, the instructions comprising:
   directing a pulsed radio frequency (RF) signal into the formation, the pulsed RF signal configured to detect an earth formation layer;
   acquiring a NQR signal from the formation; and
   interpreting the NQR signal to determine the properties of the earth formation layer.

16. The computer program product as in claim 15, wherein interpreting comprises determining a noise component in the NQR signal.

17. The computer program product as in claim 15, wherein interpreting comprises determining a radial sensitivity function (S) in relation to distance from a borehole.

* * * * *